(12) United States Patent
Groves et al.

(10) Patent No.: US 8,962,344 B2
(45) Date of Patent: Feb. 24, 2015

(54) MEMBRANE-COATED PARTICLES

(75) Inventors: John T. Groves, Berkeley, CA (US); Jeremy T. Blitzer, Sunnyvale, CA (US)

(73) Assignee: Synamem Corporation, Burlingame, CA (US)

( * ) Notice: Subject to any disclaimer, the term of this patent is extended or adjusted under 35 U.S.C. 154(b) by 958 days.

(21) Appl. No.: 12/922,993

(22) PCT Filed: Mar. 16, 2009

(86) PCT No.: PCT/US2009/037317
§ 371 (c)(1),
(2), (4) Date: Dec. 7, 2010

(87) PCT Pub. No.: WO2009/117370
PCT Pub. Date: Sep. 24, 2009

(65) Prior Publication Data
US 2011/0097819 A1   Apr. 28, 2011

Related U.S. Application Data

(60) Provisional application No. 61/036,966, filed on Mar. 16, 2008.

(51) Int. Cl.
*G01N 33/543* (2006.01)
*G01N 33/567* (2006.01)

(52) U.S. Cl.
CPC ........ *G01N 33/54313* (2013.01); *G01N 33/567* (2013.01)
USPC ............. 436/518; 435/7.2; 436/523; 436/532

(58) Field of Classification Search
None
See application file for complete search history.

(56) References Cited

U.S. PATENT DOCUMENTS

2003/0207271 A1* 11/2003 Holwitt et al. .................... 435/6
2005/0059095 A1   3/2005 Yang et al.

FOREIGN PATENT DOCUMENTS

| WO | WO 2005/006960 A | | 1/2005 | |
|----|------------------|---|--------|---|
| WO | WO 2005/057217 | * | 6/2005 | .......... G01N 33/567 |
| WO | WO 2009/117370 A1 | | 9/2009 | |

OTHER PUBLICATIONS

Sigma-Aldrich, Proteas inhibitor Cocktail for use with mammalian ceall and tissue extracts, Product Information, Catalog No. P8340, Jul. 2003, p. 1).*
International Search Report from PCT Patent Application No. PCT/US2009/037317, mailed Jun. 18, 2009.
Scott, et al., "Synexin binds in a calcium-dependent fashion to oriented chromaffin cell plasma membranes", Febs Lett., vol. 180, No. 1, p. 17-23 (1985).

* cited by examiner

*Primary Examiner* — Gary W Counts
(74) *Attorney, Agent, or Firm* — Jacqueline F. Mahoney; McDermott Will & Emery LLP

(57) ABSTRACT

A membrane-coated particle composition and methods comprising a particle surrounded by a native cell membrane are disclosed. The cell membrane may contain selected receptors or binding components. At least a portion of the receptors or binding components are oriented on the membrane-coated particle in the same or similar orientation as in the native cell membrane. The membrane-coated particle(s) finds use, for example, in contexts of basic research, proteomics, drug discovery, drug delivery, medical diagnostics, and aspects of patient care.

14 Claims, 6 Drawing Sheets

MEMBRANE-COATED PARTICLES

CROSS-REFERENCE TO RELATED APPLICATIONS

This application is a national stage entry under 35 U.S.C. §371 of PCT/US09/37317 filed Mar. 16, 2009, which claims the benefit of priority from U.S. Provisional Application No. 61/036,966, filed Mar. 16, 2008, which is incorporated in its entirety herein by reference.

TECHNICAL FIELD

A type of particle coated with a cell membrane for use in contexts including but not limited to basic research, proteomics, drug discovery, drug delivery, medical diagnostics, and aspects of patient care is described.

BACKGROUND

Cell membrane proteins represent the targets of more than 60% of pharmaceuticals currently on the market, including asthma medications (e.g. inhaled albuterol which targets membrane "fight-or-flight" receptors), cancer therapies (e.g. Herceptin which targets membrane growth factor receptors), and dermatologic agents (e.g. Raptiva which targets membrane cell adhesion molecules). To identify drugs and increase the likelihood of eventual efficacy, there has been intense interest in the development of high throughput, high information-content assays for screening drug candidates against membrane proteins in the context of their native cell membrane environment. Traditional methods have relied on expressing target proteins in live cells and performing binding assays with libraries of drug candidates. While elegant in theory, these live cell assays are somewhat labor-intensive and require expertise in cell culture. Moreover, cell-to-cell variation in both target protein expression and binding efficiency of drug candidates makes these assays essentially semi-quantitative. Variation in the size and shape of cells also makes them somewhat problematic for certain instrument detection systems.

The inherent complexity of live cell assays has stimulated the development of technology for performing high throughput, high information-content assays of cell membrane activity under in vitro conditions. A number of technologies have focused on ways of displaying cell membranes in an in vitro environment under conditions which preserve the function of cell membrane components. The MembraneChip™, developed by Synamem Corporation (U.S. Pat. No. 6,699,719; U.S. Pat. No. 6,228,326; Groves et al. (1997) *Science*, 275, 651-653) is a surface detector device for arraying phospholipid membranes that consists of planar lipid bilayer membranes (either synthetic or native cell membranes) arrayed on fused silica, which is particularly useful for high throughput parallel assays including ligand/receptor interactions and live cell-cell signal transduction (Yamazaki et al. (2005) *BMC Biotechnol.*, 5:18). This technology is predicated upon the observation that small unilamellar vesicles (SUVs), liposomes having diameters ranging from 25 nm to 5 μm, fuse with glass or silica in a manner which generates planar lipid bilayers (Brian and McConnell (1984) *Proc. Natl. Acad. Sci. U.S.A.*, 81:6159-6163; Groves and Boxer (2002) *Acc. Chem. Res.*, 35:149-157). Arrayed membranes retain a physiological level of fluidity characteristic of the in vivo environment, a property critical for numerous receptor interactions and signal transduction pathways including G protein-coupled receptor (GPCR), receptor tyrosine kinase, and T cell receptor signaling.

In a manner analogous to displaying supported lipid bilayers on planar substrates, it is also possible to deposit a single lipid bilayer (e.g. comprising dimyristoyl phosphatidylcholine (DMPC)) on commercially-available glass or silica beads (1-50 μm in diameter) (Bayer) and Bloom, (1990) *Biophys. J.*, 58:357-362). As in the case of the MembraneChip™, these membrane-derivatized beads display physiologically fluid lipid bilayers. Membranes are typically separated from the silica bead by a thin film of water as they are with planar substrates, facilitating the long-range lateral mobility of lipids and bilayer components. Membrane-derivatized beads have great utility for measuring processes ranging from ligand/receptor binding to complex cell-cell interactions. Moreover, the phenomenon of pair-wise interactions among beads in a batch has been leveraged to generate label-free assays of ligand/receptor interactions (Baksh et al. (2004) *Nature*, 427:139-141). Indeed, cholera toxin B binding to ganglioside GM1 displayed in membrane-derivatized beads has been detected using the statistical analysis of colloidal pair-wise distribution (Baksh et al. 2004).

There have been a number of studies using beads for isolating cell membranes for purposes of purification (Jacobson and Branton, (1977) *Science*, 195:302-304; Cohen et al. (1977) *J. Cell Biol.*, 75:119-134; Kinoshita et al. (1979) *J. Cell Biol.*, 82:688-696). However, these approaches invariably lead to beads coated with native cell membranes which are in an orientation with the extracellular leaflet closest to the bead surface and the intracellular leaflet exposed to the bulk solution, rendering potential membrane components on the external leaflet inaccessible to various probes. Given that quite a number of test agents and drug candidates interact with the extracellular domains of cell membrane proteins, this limitation makes it particularly challenging to use these earlier methods for investigating cell surface proteins, as well as other cell membrane components. Indeed, more recent results using erythrocyte membranes on silica beads demonstrated similar results (Kauffmann and Tanaka, (2003) *Chemphyschem*, 4:699-704), suggesting the difficulty in obtaining beads coated with membranes capable of displaying the external leaflet of the plasma membrane. These earlier methods thus generate membrane-coated particles in which the internal side of the cellular membrane is exposed to the bulk phase as opposed to the more desirable orientation whereby the external side of the membrane is exposed. Consequently, the present methods and compositions enable a considerably more useful orientation of the cell surface on a bead particle, as well as a more practical solution for in vitro analysis of cell membrane components.

Given the vast market opportunity for drugs targeting cell membrane components, there remains a tremendous need for developing technology for displaying native cell membranes in such a manner as to mimic the natural orientation of cellular membrane components on a variety of supports to enable rapid, high throughput, high information-content assays.

BRIEF SUMMARY

In one aspect, a particle coated with a cell membrane is described. The membrane coated particle may have one or more of the following properties: 1) the cell membrane is in an orientation on the particle which mimics the natural orientation of a cell membrane, in that the external leaflet of the membrane is closest to the bulk phase (outside, containing the test agents) and the internal leaflet of the membrane is closest to the surface of the bead particle; 2) a rigorously quantitative characterization of the protein content of the cell membranes displayed in an individual and/or a batch of particles; 3) a uniformity of protein abundance in cell membranes displayed on each particle in a batch; 4) similar or identical geometric configuration of the particles in a batch. Membrane-coated particles represent a batch of substantially similar or nearly identical cell membrane displays in which the identity of the proteins, as well as the precision of protein composition and shape of the particles, are critical features which enable assays utilizing high throughput, automated readouts.

In another aspect, a composition comprising a particle having an exterior surface, a coating comprising membrane portions of lysed whole cells at least partially surrounding the particle; and at least one component associated with the membrane portions is contemplated. The component will typically have a binding affinity for a ligand upon contact with the component. In embodiments, at least a portion of the membrane portions are in the same external orientation in the coating as in native cell membranes or whole cells. In an embodiment, at least 90% of at least one component is in the same external orientation as that of the native cell membrane. In other embodiments, at least 80% of at least one component is in the same external orientation of that of the native cell membrane. In yet other embodiments, at least 70%, 60%, 50%, 40%, 30%, 20%, 10% or 5% of at least one component is in the same external orientation as the native cell. The particle may be spherical. In embodiments, the particle comprises a material selected from silica, glass, borosilicate glass, polystyrene, polymethylmethacrylate, metal, semiconducting material, and organic material. The particle may comprise a material that is non-porous, porous, or mesoporous. In some embodiments, the particle is doped with a positively or negatively charged ion. In other embodiments, the particle is coated with functional amine silanes.

It will be appreciated that membrane portions may be selected from extracellular faces of an extracellular membrane, cytoplasmic faces of the extracellular membrane, and/or intracellular membranes. In one embodiment, the membrane portions comprise a single bilayer.

In embodiments, the component is selected from a protein, a lipid, and a carbohydrate. In other embodiments, the component has binding affinity for the ligand, which is selected from a small molecule, a biomolecule, a peptide, a protein, an antibody, a plasma membrane vesicle, a cell surface, a liposome, a lipid, and/or a carbohydrate.

In another aspect a system is contemplated that comprises a plurality of the compositions.

In yet another aspect, a kit comprising a packaged composition comprising a plurality of particles each having an exterior surface coated with membrane portions of lysed whole cells is contemplated. In an embodiment, the membrane portions comprise at least one component having binding affinity for a ligand upon contact with at least one component. In another embodiment, the plurality of particles is contained within a first container and the membrane portions of lysed whole cells comprising at least one component having binding affinity for a ligand upon contact of at least one component with the ligand are contained within a second container. In this embodiment, mixing of the first and second containers generates a plurality of membrane-coated particles each having an exterior surface coated with membrane portions of lysed whole cells and comprising at least one component.

In a further aspect a method comprising preparing a membrane-coated particle comprising a particle having an exterior surface, coated with membrane portions of lysed whole cells, the membrane portions comprising at least one component capable of binding a ligand upon contact under binding conditions, contacting the particle with a labeled ligand under binding conditions, and detecting the presence of the labeled ligand bound to the component is contemplated. In an embodiment, at least a portion of the membrane components are in the same orientation on the particle as in the native cell membrane. In an embodiment, the particle is spherical. In embodiments, the membrane portions are formed from extracellular faces of an extracellular membrane, cytoplasmic faces of the extracellular membrane, and/or intracellular membranes. In other embodiments, the membrane portions comprise a single bilayer on the particle.

In one embodiment, the component is selected from a protein, a lipid or a carbohydrate. In other embodiments, the component has binding affinity for the ligand, which is selected from a small molecule, a biomolecule, a peptide, a protein, an antibody, a plasma membrane vesicle, a cell surface, a liposome, a lipid, and/or a carbohydrate.

In an embodiment, the contacting step comprises contacting a plurality of membrane-coated particles. In another embodiment, the method further comprises quantifying elements selected from the labeled ligand, the component, the plurality, and/or the whole lysed cells. In yet another embodiment, the quantifying step comprises ascertaining a level of an element with a variability on an order of a square root of the level.

In embodiments, the plurality of membrane-coated particles are of a uniform size.

In another aspect a method of preparing particles coated with cellular membranes is contemplated. The method comprises lysing whole cells having a cell membrane component of interest and harvesting the cellular membranes, sonicating the harvested cellular membranes; and mixing the sonicated cellular membranes with coating solution and beads.

BRIEF DESCRIPTION OF THE FIGURES

FIG. 1A shows membrane-coated particles stained with the styryl dye FM® 1-43FX (Left: Bright-field, Right: Fluorescence). FIG. 1B shows bare silica stained with the styryl dye FM® 1-43FX (Left Bright-field, Right: Fluorescence). FIG. 1C and FIG. 1D show the membrane-coated particles and bare silica, respectively, without staining (Left: Bright-field, Right: Fluorescence).

FIG. 2A shows membrane-coated particles incubated with ALEXA FLUOR® 488-conjugated transferrin (Left: Bright-field, Right: Fluorescence). FIG. 2B shows membrane-coated particles incubated with ALEXA FLUOR® 488-conjugated transferrin in the presence of excess unlabeled transferrin (Left: Bright-field, Right: Fluorescence). FIG. 2C shows bare silica incubated with ALEXA FLUOR® 488-conjugated transferrin (Left: Bright-field, Right: Fluorescence). FIG. 2D shows membrane-coated particles alone. FIG. 2E shows differential fluorescence quantitation of the data in FIG. 2A-2D.

DETAILED DESCRIPTION

A. Membrane-Coated Particles

Figure 1A:
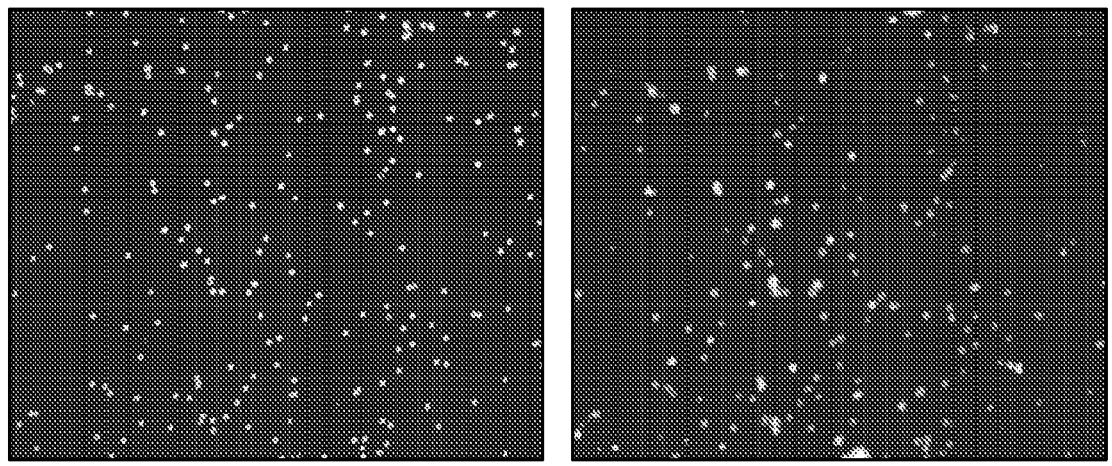
FIGS. 1A-1D show membrane-coated particles prepared from Chinese Hamster Ovary (CHO) membranes and silica beads.
Figure 1B:
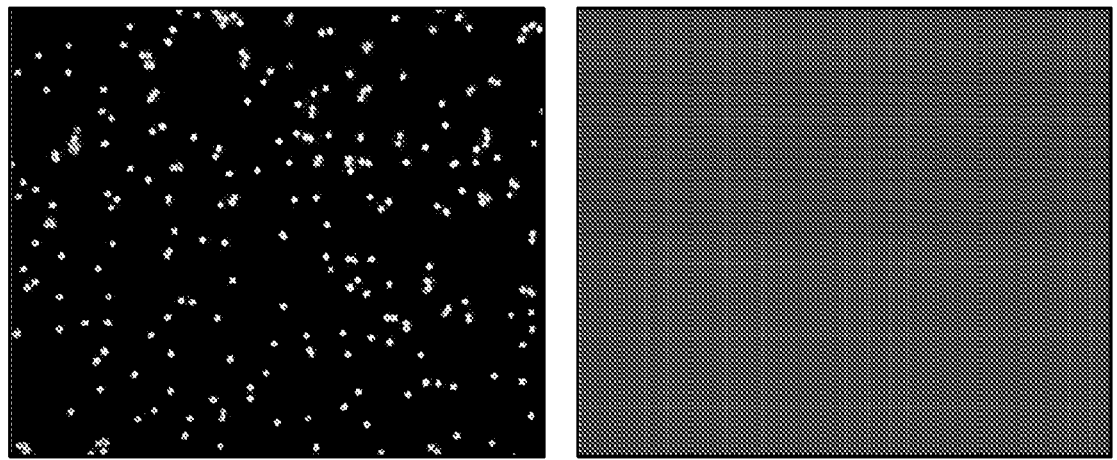

The membrane-coated particle is generally a particle, such as a bead, coated with a membrane derived from a whole, intact cell. In this manner, the membrane-coated particles consist of beads displaying nearly all aspects and elements of the plasma membrane and intracellular membranes in a manner accessible to binding and/or targeting. For example, components of the lipid membrane mimic the orientation found on the native cell with components that naturally face the external environment on the outside of the membrane-coated particle (facing the bulk phase) and components that naturally face the cytosol of the cell on the inside of the lipid bilayer particle (facing the surface of the bead particle). Those membrane components that face the external environment would be accessible to probes and test agents, such as antibodies specific to the extracellular domain of a membrane component, such that the relative orientation of the membrane components can be determined. In one embodiment, the lipid-membrane particle comprises (a) membrane component(s) at least 90% in the same external orientation as in the native cell. In another embodiment, the membrane component(s) on the lipid-bilayer particle is at least 80% in the same external orientation as in the native cell. In still another embodiment, the membrane components of the lipid-bilayer particle are at least 70%, 60%, 50%, 40%, 30%, 20%, 10% or 5% in the same external orientation as the native cell. It will be appreciated that the percentage of membrane component(s) will be in the same external orientation as in the native cell, such as 5-90% of the membrane component(s) being in the same external orientation as in the native cell. Numeric ranges are inclusive of the numbers defining the range. The percentage of a membrane component displayed in the same external orientation as in the native cell can be determined by any method known in the art. In an exemplary embodiment, the percentage is determined by comparing the amount of the surface density of a specific membrane component (e.g. a transmembrane protein such as a GPCR, an ion channel, or an adhesion protein such as ICAM-1) on a native intact cell with that on a membrane-coated particle generated using membranes from an identical cell, e.g. same cell line.

The percentage or amount of membrane component displayed in the same external orientation as in the native cell can be increased by enriching for this desired orientation at the SUV formation stage following homogenization of lysed cells. As described further below, following homogenization, the SUVs formed represent various orientations of the cell membrane (outside-out and inside-out). By way of example and without limitation, one of the methods which could be used to enrich for SUVs displaying the membrane component in the same external orientation as in the native cell (which could then be used immediately to coat particles with the desired external orientation for the membrane component), could be immunoaffinity chromatography to isolated SUVs displaying externally-exposed membrane component. In the event that membranes from intracellular organelles (e.g. endoplasmic reticulum, Golgi complex, and mitochondria) are desired, SUVs derived from these organelles could be obtained using standard differential centrifugation approaches. An analogous process of immunoaffinity purification could be used to enrich for organelle-derived SUVs of the appropriate orientation using antibodies directed against various components of these organelle membranes. Moreover, membrane-coated particles may be formulated as a standardized biochemical reagent, and could thus be thoroughly characterized in the quantity of membrane proteins present. The membrane-coated particle may preferably be strictly uniform in geometry and protein content, or both. Consequently, membrane-coated particles combine the advantages of a cell membrane having a full complement of proteins with the simplicity of an in vitro system, altogether avoiding the complexity and variability of live cells. In this way, the uniformity of membrane-coated particles enables their use in numerous automated detection schemes.

Figure 3A:
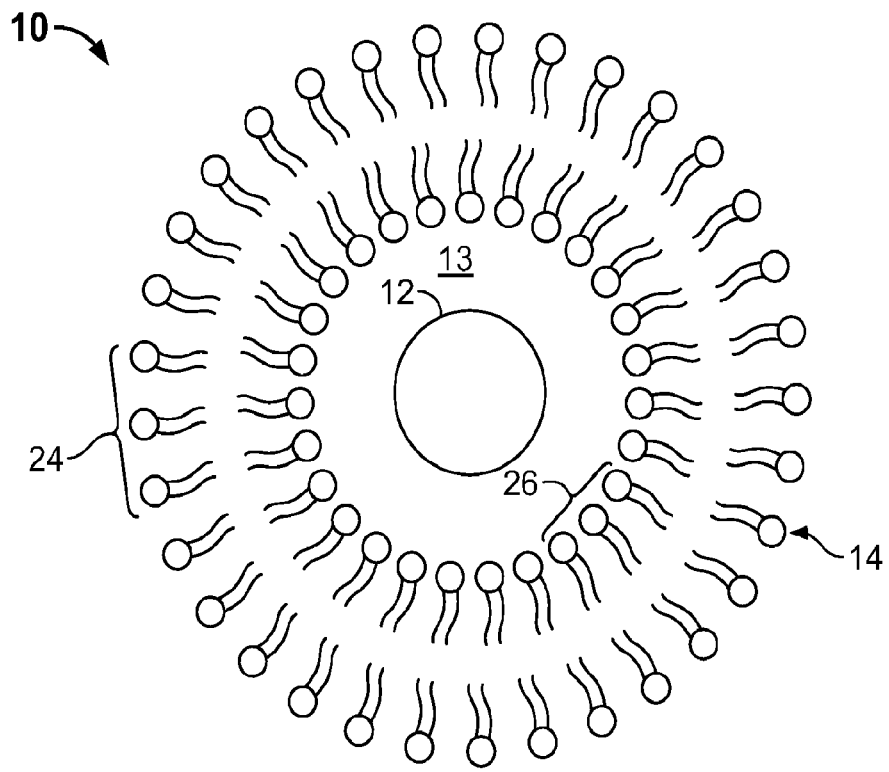
FIGS. 3A-3B are schematics of exemplary membrane-coated particles.
Figure 3B:
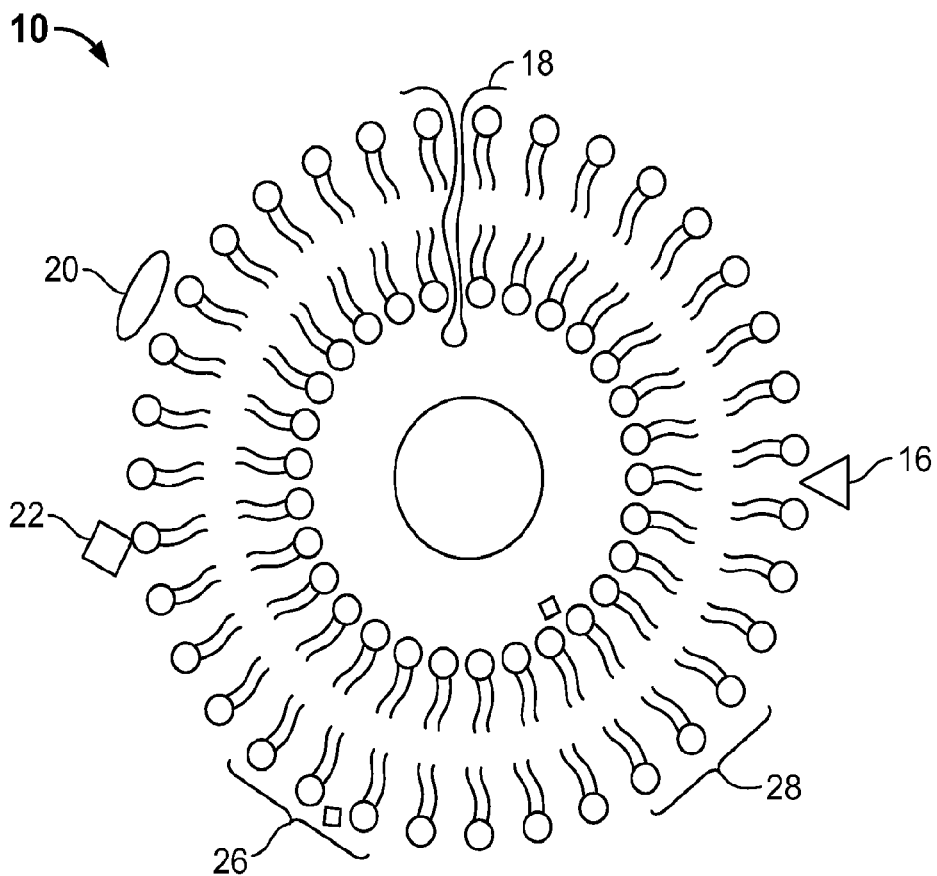

In one aspect, membrane-coated particles 10 are batches of beads covered or coated with cell membranes. Preferably, both the extracellular and intracellular leaflets of the membrane are readily accessible to targeting with biological reagents. As seen in FIGS. 3A and 3B, the particle comprises a bead 12 at least partially surrounded by a native or whole cell membrane 14. The beads may be composed of a variety of materials, including but not limited to silica, glass, borosilicate glass, polystyrene, polymethylmethacrylate, as well as nanoparticles (e.g. metallic, semiconducting, or organic). It will be appreciated that the bead may be composed of a single or more than one material. Preferably, the beads are formed from any bilayer-compatible material. In another embodiment, at least the outer surface of the beads are formed of a bilayer-compatible material. Methods for determining the suitability of a material for use as a bilayer-compatible material are known in the art and detailed in U.S. Pat. No. 6,228, 326.

In one embodiment, the particles or beads are obtained from a commercial source such as Bangs Laboratories (Fishers, Ind.). In yet another embodiment, the beads are manufactured according to known methods for preparing beads to the necessary specifications. The beads may be cleaned and/or sterilized by any suitable method as known in the art. In one embodiment, the beads may be cleaned overnight in 6-Molar sodium hydroxide (NaOH). In another embodiment, the beads may be heated to a temperature suitable to clean and/or sterilize the beads, acid washed with, for example pirrhana solution acid wash (3:1 $H_2SO_4:H_2O_2$), and immersed in detergent, for example 7x detergent available from ICN Biomedicals, Inc.

The beads may be doped with any of a number of different positively- or negatively-charged ions in order to assist with coating of the beads. In another embodiment, the beads may be doped with various rare earth elements (e.g. lanthanides) in the membranes (Dejneka et al. (2003) *Proc. Nail. Acad. Sci. U.S.A.,* 100:389-393). In yet another embodiment, the beads may be pre-coated with functional amine silanes to enhance stability of deposited membranes. In one embodiment, the beads are spherical. In other embodiments, the beads can be any suitable geometric shape, including, but not limited to spheroid, ovoid, polygonal, cylindrical, etc. In another embodiment, all beads in a batch are of the same or similar geometric shape. In other embodiments, the beads are geometrically identical or substantially similar. Beads typically measure in colloidal dimensions of 1-50 μm in diameter, although nanoparticle size (50 nm to 1 μm) and larger (up to 1 mm) size is also contemplated.

The native, whole cell membranes deposited on the beads are preferably derived from homogenates of total cellular particulate fractions. In one embodiment, the native cell is a wild-type cell. These membranes may be derived from a variety of standard lines of cultured cells, including but not limited to HEK-293, CHO, COS-7, and HeLa, as well as cells derived from blood or organ tissue. Membranes may also be derived from non-mammalian cells, including, but not limited to, yeast, as well as prokaryotic cells, including but not limited to various bacterial strains. The cell membranes may also be derived from pathological tissues, including but not limited to tumors and cancer cells. Membranes may also be derived from cells which are either transiently or stably expressing proteins of interest, which may or may not normally be expressed in these particular cell lines. By way of example and without limitation, membrane-coated particles are generated from CHO cells expressing a receptor (e.g. a GPCR or RTK), a cell adhesion molecule (e.g. ICAM-1), or an ion channel (e.g. a potassium channel).

In a specific embodiment, total cellular membranes are prepared from homogenization of lysed cells, followed by probe sonication to obtain SUVs sufficient for fusion and display as single lipid bilayers on the beads. Indeed, the size of the total cellular membrane vesicles can be critical for obtaining physiological single bilayer dimensions, as vesicles of larger sizes would generate multilamellar membranes which lack physiological relevance. Alternatively, appropriate vesicles could be formed by mixing detergent-solubilized membrane components with synthetic vesicles and removing the detergent through dialysis. The resulting membrane-coated particle consists of lipid bilayers comprising membrane portions representing the plasma membrane. The membrane-coated particle may also comprise various intracellular organelle membranes. These intracellular organelle membranes are preferably oriented such that both their extracellular and cytoplasmic faces are accessible to probing with numerous ligands and test agents. As described above, the membrane-coated particles may be enriched for membrane-coated particles displaying membrane components with the desired orientation. At least a portion of the membrane portions 24 have the same orientation as in whole cells. It will be appreciated that some membrane portions may have the same orientation as in whole cells 26, while others may have the opposite orientation as in whole cells 28. By opposite orientation, it is meant that membrane components that would be oriented external to the cellular compartment in the whole cell are internal and face the particle. In one embodiment, at least 90% of the membrane portions in the coating surrounding the particle have the same external orientation as in the native cell. In another embodiment, at least 80% of the membrane portions are in the same external orientation as in the native cell. In still another embodiment, at least 70%, 60%, 50%, 40%, 30%, 20%, 10% or 5% of the membrane portions are in the same external orientation as the native cell. Numeric ranges are inclusive of the numbers defining the range.

The bilayer coating may include various cell membrane components associated with the bilayer (16, 18, 20, and 22 in FIG. 3B). Various components of the cell membranes displayed on membrane-coated particles may be probed and characterized. The components may be selected from any native membrane component, including, but not limited to receptors, proteins and peptides, and carbohydrates. As shown in FIG. 3B, the component may be integral or transmembrane 18, anchored to the lipid 22, or peripheral 20. These components consist of macromolecules from a number of categories, including proteins, lipids, carbohydrates, as well as various combinations of each. Membrane components amenable to be probed may be those which are expressed endogenously in the cell lines, as well as those which are over-expressed with various molecular biological reagents. By way of example and without limitation, the cell adhesion protein ICAM-1 may be over-expressed and displayed in the cell membrane through fusion of a C-terminal glycosylphosphatidylinositol anchoring moiety (WO 2005/078104; Yamazaki et al. 2005).

Cell membrane components displayed on the membrane-coated particles are preferably readily accessible, in that they are free to bind various test agents or ligands, including but not limited to small molecules, biomolecules, peptides, proteins, antibodies, vesicles derived from the plasma membrane or liposomes. Binding of these various agents and ligands to membrane components present on the membrane-coated particles may be detected through their derivatization with a number of detectable moieties, including but not limited to fluorophores and radioisotopes. In addition, other detection schemes could exploit the intrinsic properties of the particles themselves, including but not limited to fluorescence, colloidal distribution, scatter, plasmon resonance, and magnetics.

In one embodiment, the cell membrane layer is separated from the bead by an aqueous film 13. Aqueous refers generally to a water-based liquid medium. The aqueous film may be any suitable aqueous solution, including, but not limited to, a buffered saline solution (e.g. PBS). Preferably, the aqueous film is not deleterious to lipids, membrane components and/or the components of the beads. The aqueous film is preferably between about 5 Å and 15 Å (typically about 10 Å) in thickness. The aqueous film may contribute to the long-range lateral fluidity of transmembrane proteins. In one embodiment, the aqueous film is about 1 nm thick.

Figure 1C:
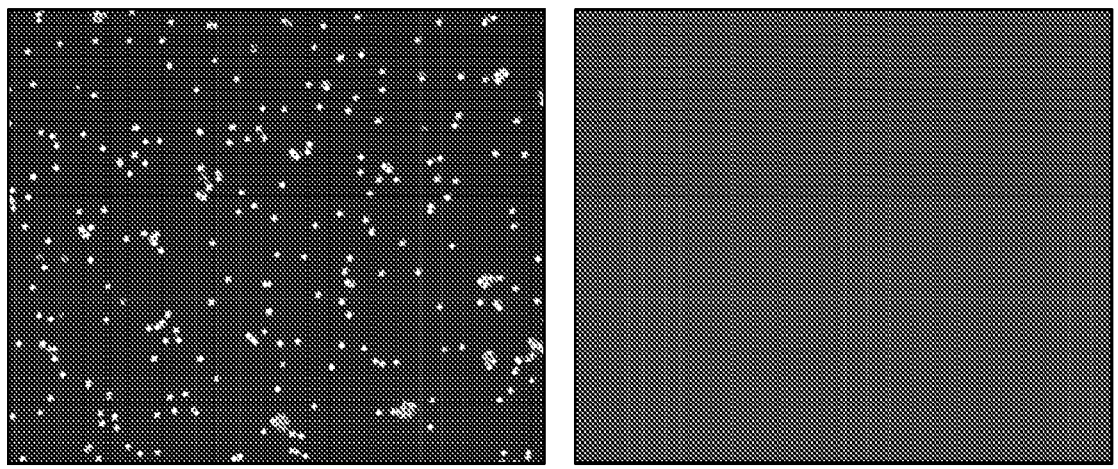
Figure 1D:
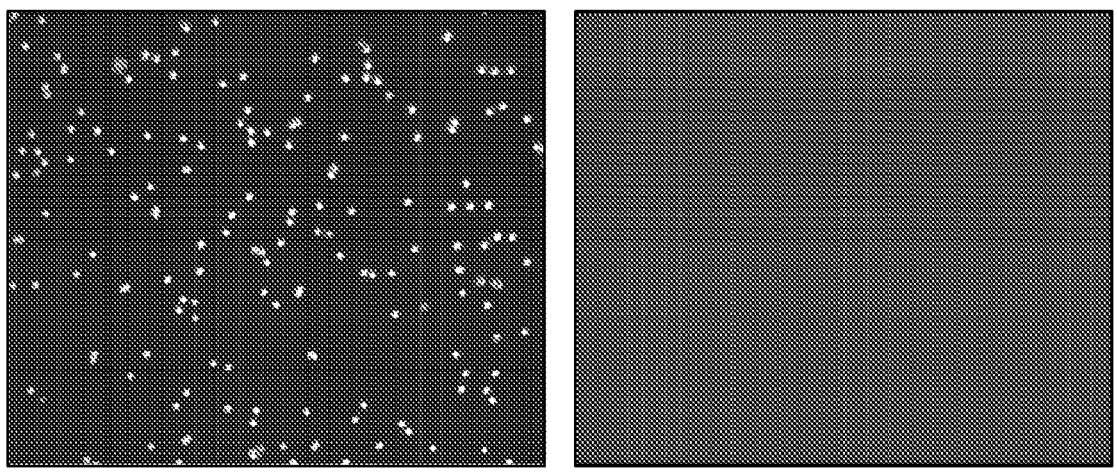

According to experiments performed in support of the invention, as detailed in Example 1, membrane-coated particles were generated from CHO cell membranes and hydrophilic silica microspheres. FIG. 1 demonstrates representative results from coating silica beads with CHO cell membranes. As shown in FIG. 1A (Left: Bright-field, Right: Fluorescence), staining of membrane-coated particles is highly efficient. FM® 1-43FX staining is specific for particles coated with membranes, as silica beads devoid of membranes exhibit very little staining (see FIG. 1B; Left: Bright-field, Right: Fluorescence). Moreover, membrane-coated particles and bare silica exhibit very little background auto-fluorescence (as shown in FIG. 1C and FIG. 1D; Left: Bright-field, Right: Fluorescence). Consequently, membrane-coated particles are generated in a very efficient manner, and are readily amenable to quality control and quality assurance steps (e.g. FM® 1-43FX staining) for monitoring membrane coating effectiveness and efficiency.

Figure 2A:
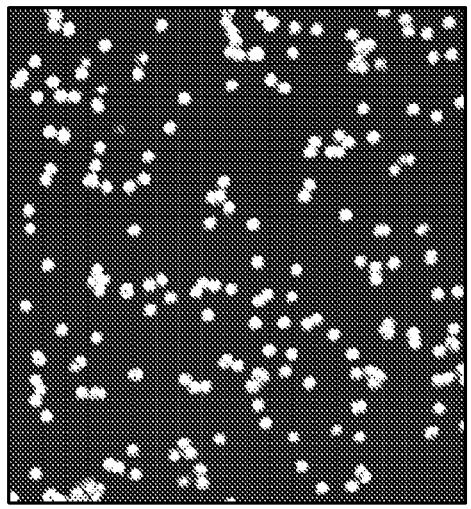
FIGS. 2A-2E show binding of transferrin to its receptor using membrane-coated particles.
Figure 2A:
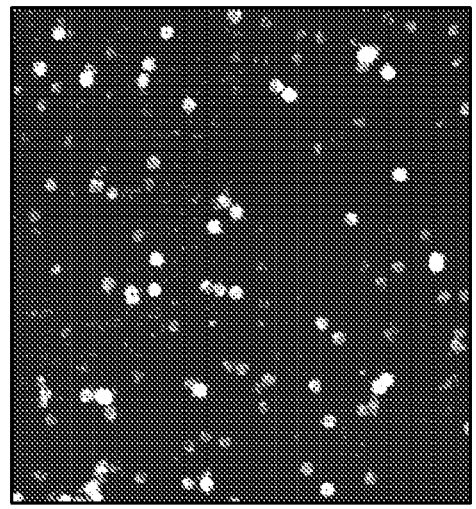
Figure 2B:
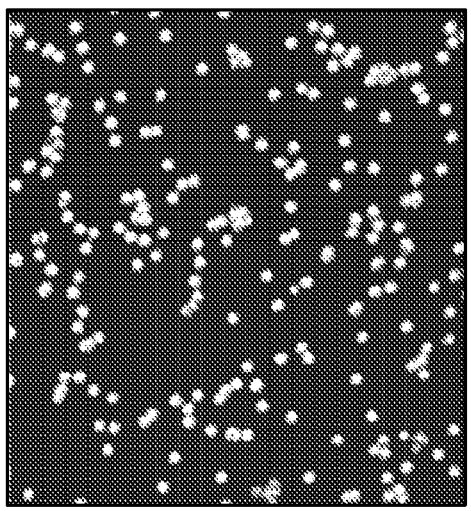
Figure 2B:
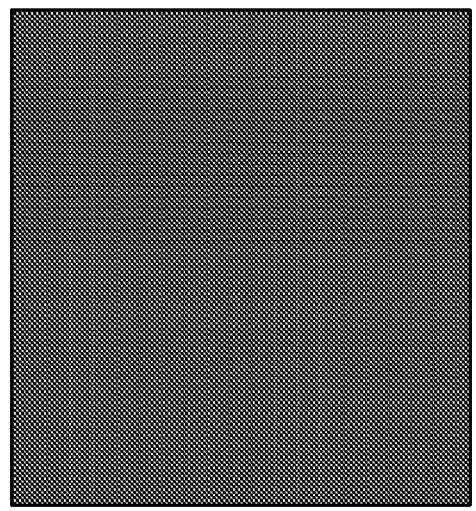
Figure 2C:
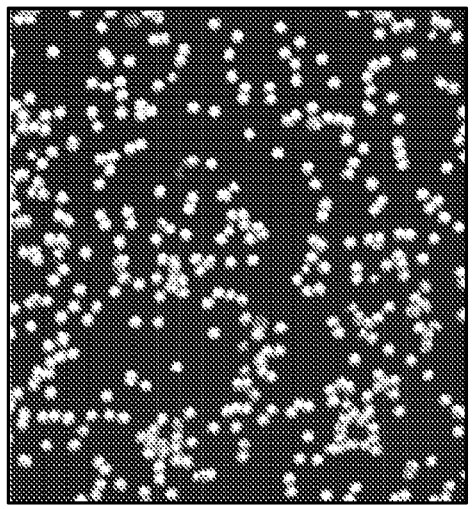
Figure 2C:
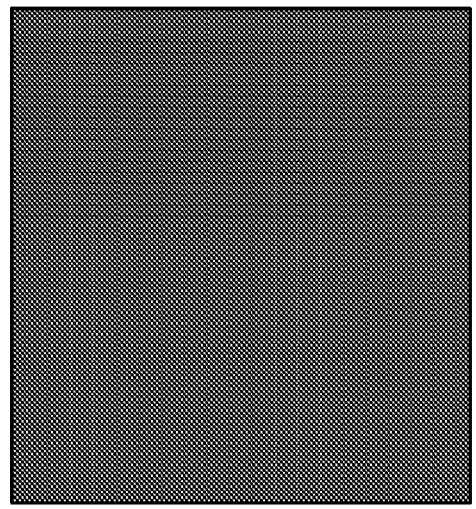
Figure 2D:
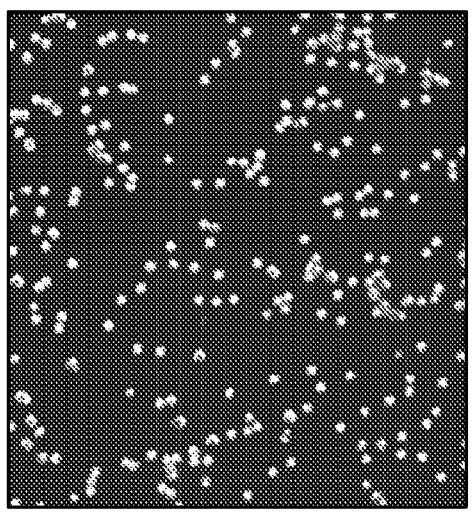
Figure 2D:
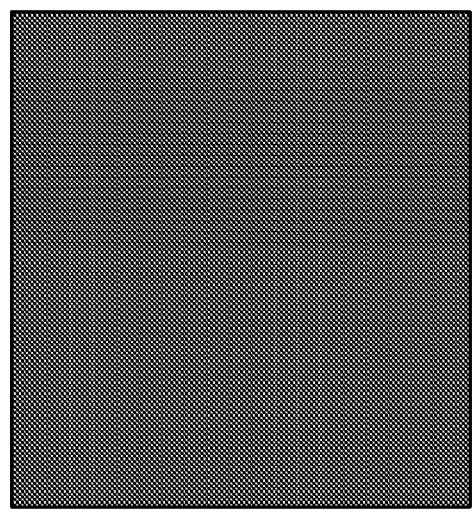
Figure 2E:
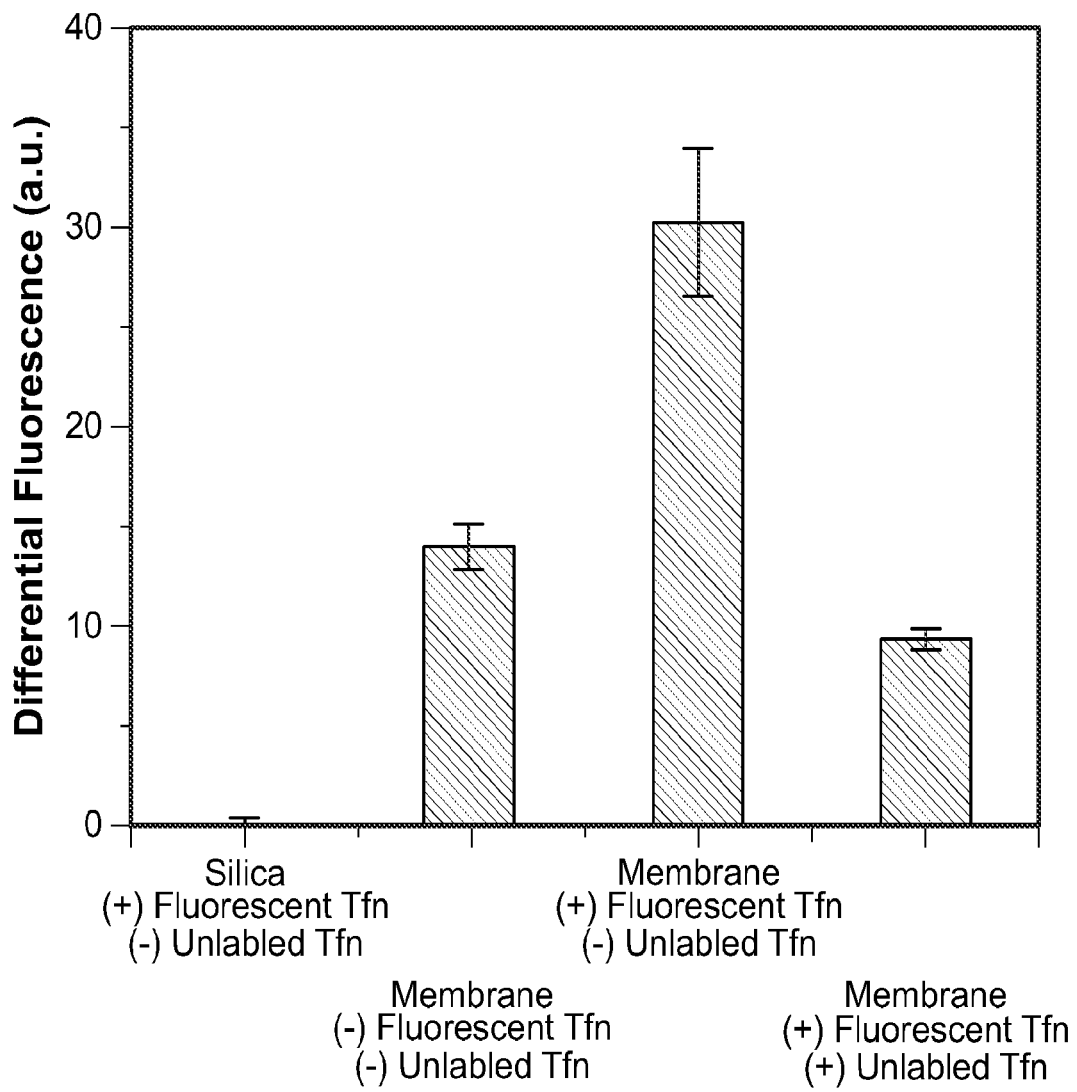

Ligand/receptor interactions were investigated as described in Example 2, showing fluorescently-labeled transferrin binding to the endogenously-expressed transferrin receptor present on the membrane-coated particles (see FIGS. 2A-2E). Fluorescently-labeled transferrin binds efficiently to the membrane-coated particles (see FIG. 2A; Left: Bright-field, Right: Fluorescence). As would be expected if the process is specific and saturable, the transferrin binding was readily competed away with a 100-fold molar excess of unlabeled transferrin (FIG. 2B; Left: Bright-field, Right: Fluorescence). Moreover, the lack of staining as seen in FIG. 2C (Left: Bright-field, Right: Fluorescence) demonstrates that fluorescently-labeled transferrin does not interact appreciably with bare silica (devoid of membranes). Lastly, in the absence of a fluorescent ligand, the membrane-coated particles exhibited minimal background auto-fluorescence on microscopy (FIG. 2D; Left: Bright-field, Right: Fluorescence). FIG. 2E shows a quantitation of the ligand binding experiment using a 96-well fluorescence plate reader.

B. Methods of Use

Identifying novel receptor antagonists has been a major theme in drug discovery, and has traditionally been performed using radioactively-labeled ligands and whole cells. Given the extensive accessibility of membrane proteins on membrane-coated particles found with the present membrane-coated particles, this technology represents an ideal solution to the complexity of radioligand binding assays on live cells.

Membrane-coated particles are also contemplated for use in the field of immunology drug discovery, as they could display various adhesion molecules (e.g. ICAM-1). Adhesion ligands are conjugated with a fluorescent dye, and their binding to cognate molecules on membrane-coated particles is measured in a highly quantitative fashion. Binding assays are performed in the presence of candidate drugs in order to identify those which antagonize ligand binding. While blocking these interactions would be expected to interfere with the ability of immune system cells to migrate to sites infection, such an event could be quite efficacious in situations where the immune system is overactive, as in various autoimmune diseases (e.g. multiple sclerosis, psoriasis, Crohn's disease, and rheumatoid arthritis).

A number of disease states, particularly various cancers, feature the up-regulation or over-expression of specific membrane proteins. Aberrantly high expression of Her2, for example, is thought to facilitate the malignant pathogenesis of breast and ovarian tumors (Moasser (2007) *Oncogene* (Epub ahead of print)). Indeed, the presence of Her2 in breast tumors predicts aggressive activity and confers a poor prognosis. However, in addition to predicting clinical outcome, expression of Her2 renders the tumors susceptible to therapy with the monoclonal anti-Her2 antibody Herceptin. In the case of acute myeloid leukemia, the cell surface protein CD33 has become of particular interest, as it is the target for the monoclonal antibody therapy Mylotarg (an anti-CD33 monoclonal antibody). As these examples indicate, knowledge of the quantitative levels of particular membrane proteins confers critical information with regard to diagnostic, therapeutic, and prognostic considerations.

Membrane-coated particles also represent a powerful technology for quantifying the expression of various membrane proteins associated with diverse disease states, including but not limited to cancer and autoimmunity. By way of example and without limitation, a simple blood sample could be isolated from a patient with a suspected leukemia. Cells from this blood sample would be used to generate membrane-coated particles of the patient's white blood cell compartment. Alternatively, membrane-coated particles could be used as quantitative standards containing known amounts of the cell surface protein of interest. Consequently, membrane-coated particles could be used as standards for quantitating membrane proteins on intact cells through fluorescence activated cell sorting (FACS) analysis, immunofluorescence microscopy, and instrument plate readers. In traditional FACS experiments, surface proteins are quantitated using generic fluorescence beads, rather than beads containing cell surface proteins of known amounts as with the membrane-coated particles technology. Known amounts of membrane components on the membrane-coated particles could be used to calibrate the FACS detection of unknown levels of these markers on patient cells (e.g. CD33 levels on AML cells). In this manner, the presence and/or over-expression of tumor specific or tumor-associated cell surface markers could readily be ascertained in a highly quantitative fashion using antibody detection. These results would be useful in the diagnosis, as well as suggest which therapies may have efficacy against, the leukemia. Moreover, serial assays of these tumor specific or tumor associated cell surface markers via membrane-coated particles could be used to monitor treatment efficacy.

GPCRs represent the largest class of cell surface receptors in mammalian cells, and regulate such diverse processes as cellular differentiation, excitability, and metabolism. They are one of the most frequently targeted classes of molecules in drug discovery. Displaying GPCRs on the membrane-coated particles affords an in vitro environment for measuring both ligand binding and receptor activation. Ligand binding to a GPCR initiates receptor binding to heterotrimeric guanine nucleotide binding proteins (G proteins) located on the inner leaflet of the plasma membrane. Subsequently, the G protein exchanges its bound GDP (maintaining the G protein in the inactive state) for a GTP, a process which causes dissociation of the G protein into $G_\alpha$ and $G_{\beta\gamma}$ subunits which can modulate various cellular effectors, including adenylyl cyclase. Traditional assays have exploited this GTP/GDP exchange as a readout of GPCR activation. Indeed, fluorescence-based analogues of GTP (Europium in this case) have been used to monitor activation of GPCRs displayed in membrane arrays on solid supports (Hong et al. (2005) *J. Am. Chem. Soc.*, 127:15350-15351). Activation of the GPCR facilitates incorporation of Europium-conjugated GTP into the G protein in a manner readily detectable by automated fluorescence readouts (Hong et al. (2005)). Such a readout of GPCR activity as described in Hong et al. (Hong et al. (2005)) is also compatible with GPCRs displayed on membrane-coated particles. Another assay of GPCR activation measures the dissociation of heterotrimeric G proteins into $G_\alpha$ and $G_{\beta\gamma}$ subunits through fluorescence resonance energy transfer (FRET) (Azpiazu and Gautam (2004) *J. Biol. Chem.*, 279:27709-27718). Inactive G proteins generate FRET given the close apposition of their tightly-bound subunits. By contrast, ligand-induced GPCR activation leads to dissociation of the G protein subunits, thereby hindering their ability to achieve FRET. Given the accessibility of both outer and inner leaflets of the plasma membranes displayed on membrane-coated particles, assays of GPCR activation similar to these could be highly enabling.

C. EXAMPLES

The following examples illustrate various aspects of making and using the membrane-coated particles described herein. They are not intended to limit the scope of the compositions or methods described herein.

Example 1

Generation of Membrane-Coated Particles

In this example, membrane-coated particles were generated from CHO cell membranes and hydrophilic silica microspheres (the bead particles). Coating of silica beads with CHO cell membranes was verified through specific staining with the styryl dye FM® 1-43FX (Invitrogen Corporation) and fluorescence microscopy.

Briefly, CHO cells were grown to confluence in four 175-cm² flasks. Confluent cells were harvested using Detachin (Genlantis, Inc.) cell detaching reagent, and pelleted by centrifugation. Cells were resuspended in 12 mL of lysis buffer (10 mM Tris-HCl, pH 8.0) by vortexing, and allowed to lyse for 30 minutes at 4° C. by rotation. Membranes from lysed cells were isolated by centrifugation at 3,000×g and resuspended in 3 mL of phosphate-buffered saline (PBS). Resuspended membranes were sonicated in DRAM glass vials using a stepped micro-tip probe to yield SUVs. 100 μL of SUVs were added to 100 μL of coating solution (20 mM Tris-HCl pH 7.4, 500 mM NaCl) pre-warmed to 60° C. 100 μL of this 1:1 mixture was added to 100 μL of silica beads (10% w/v) (Bangs Laboratories, Inc.), followed by pulse vortexing. Beads were pelleted by microcentrifugation, followed by resuspension in 1 mL of deionized water (pre-warmed to 37° C.). Beads were pulse-vortexed, followed by pelleting by microcentrifugation. Beads were resuspended in 975 μL of PBS.

One vial of lyophilized FM® 1-43FX, a styryl dye which becomes fluorescent upon interaction with a lipid bilayer but not in the absence of a bilayer, was resuspended in PBS to a final concentration of 200 µg/mL. 25 µL of FM® 1-43FX dye was added to beads, followed by a 2-minute incubation by rotation. Beads were washed twice with deionized water in preparation for microscopy. Beads were examined at 20× magnification (FIGS. 1A-1D) using a ZEISS® AXIOVERT® inverted fluorescence microscope with AXIOCAM® camera. As demonstrated by the specific FM® 1-43FX staining, a very high efficiency of coating of bead particles with native cell membranes was observed (FIGS. 1A-1D).

Example 2

Ligand Binding and Displacement Assays on Membrane-Coated Particles

The binding of transferrin to its receptor was studied for ligand/receptor interactions, present endogenously in membrane-coated particles derived from CHO cell membranes (Example 1). Freshly-prepared membrane-coated particles were resuspended in 1 ml of binding buffer (10 mM Tris-HCl pH 7.4, 100 mM NaCl). Beads were subsequently pelleted and resuspended in 1 ml of blocking buffer (0.1% w/v casein in binding buffer), and incubated at room temperature for 15 minutes with rotation. Beads were pelleted and resuspended in 980 µL of binding buffer. At this time, any inhibitors or antagonists (e.g. excess of unlabeled transferrin) could have been added for a pre-incubation step. ALEXA FLUOR® 488-conjugated human holotransferrin was added to the membrane-coated particles at a final concentration of 10 µg/ml, followed by incubation at room temperature for 15 minutes with rotation. Following the incubation with transferrin, the beads were washed twice with binding buffer in preparation for viewing using fluorescence microscopy (same microscope apparatus as described in Example 1). The results of the fluorescence microscopy are shown in FIGS. 2A-2E. The accessibility of membrane proteins (in this case the transferrin receptor) to interact with various ligands and test agents (in this case transferrin) is shown by the results (see FIGS. 2A-2E).

All patents and patent publications referred to herein are hereby incorporated by reference.

Certain modifications and improvements will occur to those skilled in the art upon a reading of the foregoing description. It should be understood that all such modifications and improvements have been deleted herein for the sake of conciseness and readability but are properly within the scope of the following claims.

It will be appreciated that embodiments described with respect to one aspect may be applicable to each aspect of the particle and method described. It will further be appreciated that embodiments may be used in combination or separately. It will also be realized that sub-combinations of the embodiments may be used with the different aspects. Thus, although embodiments have been described with many optional features, these features are not required unless specifically stated. It will also be realized that the particle may be used in combination with other procedures or methods as appropriate.

What is claimed is:

1. A composition comprising:
   a particle having an exterior surface,
   a coating comprising membrane portions of lysed whole cells at least partially surrounding the particle; and
   at least one component associated with the membrane portions, the component having a binding affinity for a ligand upon contact with the component;
   wherein at least 5% of said at least one component is in the same external orientation in the coating as in the whole cells; and
   wherein the membrane portions are fluidly localized above the particle exterior surface.

2. The composition of claim 1, wherein at least 90% of the at least one component is in the same external orientation as that of a native cell membrane.

3. The composition of claim 1, wherein at least 80% of the at least one component is in the same external orientation of that of a native cell membrane.

4. The composition of claim 1, wherein at least 70%, 60%, 50%, 40%, 30%, 20%, or 10% of the at least one component is in the same external orientation as a native cell.

5. The composition of claim 1, wherein the particle is spherical.

6. The composition of claim 1, wherein the particle comprises a material selected from the group consisting of silica, glass, borosilicate glass, polystyrene, polymethylmethacrylate, metal, semiconducting material, and organic material.

7. The composition of claim 1, wherein the particle comprises a material that is non-porous, porous, or mesoporous.

8. The composition of claim 1, wherein the particle is doped with a positively or negatively charged ion.

9. The composition of claim 1, wherein the particle is coated with functional amine silanes.

10. The composition of claim 1, wherein the membrane portions are selected from the group consisting of extracellular faces of an extracellular membrane, cytoplasmic faces of the extracellular membrane, and intracellular membranes.

11. The composition of claim 1, wherein the membrane portions comprise a single bilayer.

12. The composition of claim 1, wherein the component is selected from the group consisting of a protein, a lipid, and a carbohydrate.

13. The composition of claim 1, wherein the component has binding affinity for the ligand, which is selected from the group consisting of a small molecule, a biomolecule, a peptide, a protein, an antibody, a plasma membrane vesicle, a cell surface, a liposome, a lipid, and a carbohydrate.

14. A system comprising a plurality of the compositions of claim 1.

* * * * *